United States Patent
Lennon

(10) Patent No.: US 7,087,650 B2
(45) Date of Patent: Aug. 8, 2006

(54) COMPOSITION IN THE FORM OF AN OIL-IN WATER EMULSION CONTAINING A SILICONE COPOLYMER AND SHOWING A LIQUID CRYSTALLINE PHASE AND USES THEREOF

(75) Inventor: Paula Lennon, Lyons (FR)

(73) Assignee: L'Oreal, Paris (FR)

( * ) Notice: Subject to any disclaimer, the term of this patent is extended or adjusted under 35 U.S.C. 154(b) by 252 days.

(21) Appl. No.: 10/270,338

(22) Filed: Oct. 15, 2002

(65) Prior Publication Data

US 2003/0105169 A1    Jun. 5, 2003

(30) Foreign Application Priority Data

Oct. 15, 2001  (FR)  .................................. 01 13272

(51) Int. Cl.
*A61K 8/25* (2006.01)
*B01F 17/54* (2006.01)
*C08L 83/04* (2006.01)

(52) U.S. Cl. ..................... 516/55; 516/53; 106/287.16; 424/70.12; 428/447; 524/588

(58) Field of Classification Search .................. 516/53, 516/55

See application file for complete search history.

(56) References Cited

U.S. PATENT DOCUMENTS

| | | | | |
|---|---|---|---|---|
| 5,244,598 A | * | 9/1993 | Merrifield et al. | ............ 516/55 |
| 5,518,716 A | * | 5/1996 | Riccio et al. | ............... 424/70.1 |
| 5,925,469 A | * | 7/1999 | Gee | ............................ 428/447 |
| 6,013,682 A | | 1/2000 | Dalle et al. | |
| 6,235,834 B1 | * | 5/2001 | Gee et al. | .................... 524/837 |
| 6,451,298 B1 | * | 9/2002 | Decoster et al. | ......... 424/70.12 |
| 6,638,519 B1 | | 10/2003 | Lorant | |
| 2003/0031642 A1 | * | 2/2003 | Lezer | ...................... 424/70.12 |
| 2003/0068291 A1 | * | 4/2003 | Decoster et al. | ......... 424/70.12 |

FOREIGN PATENT DOCUMENTS

| | | |
|---|---|---|
| EP | 1 097 703 A1 | 5/2001 |
| WO | WO 95/28913 | 11/1995 |
| WO | WO 97/32560 | 9/1997 |
| WO | WO 97/32561 | 9/1997 |
| WO | WO 2004/024114 A2 | 3/2004 |

OTHER PUBLICATIONS

U.S. Appl. No. 10/334,979, filed Jan. 02, 2003, Lennon.
U.S. Appl. No. 10/270,338, filed Oct. 15, 2002, Lennon.

* cited by examiner

*Primary Examiner*—Randy Gulakowski
*Assistant Examiner*—Timothy J. Kugel
(74) *Attorney, Agent, or Firm*—Oblon, Spivak, McClelland, Maier & Neustadt, P.C.

(57) ABSTRACT

A composition in the form of an oil-in-water emulsion containing, in a physiologically acceptable medium, an oily phase dispersed in an aqueous phase, the aqueous phase containing particles of a noncrosslinked silicone copolymer and at least one amphiphilic surfactant capable of forming liquid crystals.

38 Claims, No Drawings

COMPOSITION IN THE FORM OF AN OIL-IN WATER EMULSION CONTAINING A SILICONE COPOLYMER AND SHOWING A LIQUID CRYSTALLINE PHASE AND USES THEREOF

FIELD OF THE INVENTION

The present invention relates to a composition in the form of an oil-in-water emulsion comprising an oily phase dispersed in an aqueous phase, the aqueous phase comprising particles of a silicone copolymer, and to the use of the composition in, e.g., the cosmetics and dermatological fields, in particular for caring for and/or treating the skin of the body or of the face, the hair and/or the lips.

BACKGROUND OF THE INVENTION

For various reasons related in particular to better comfort of use (softness, emollience and others), current cosmetic compositions are generally provided in the form of an oil-in-water (O/W) emulsion composed of a continuous dispersing aqueous phase and of a non-continuous dispersed oily phase, or of a water-in-oil (W/O) emulsion composed of a continuous dispersing oily phase and of a non-continuous dispersed aqueous phase. O/W emulsions are the most in demand in the cosmetics field because they comprise an aqueous phase as an external phase, which confers on them, during application to the skin, a fresher, less greasy and lighter feel than W/O emulsions.

Furthermore, it is known that surfactants capable of forming anisotropic lamellar phases (liquid crystals) make it possible to obtain stable emulsions which are particularly advantageous: see, in this respect, G. Dahms, Cosmetics & Toiletries, 1986, vol. 101, pp. 113–115. However, such emulsions exhibit the disadvantage of having unsatisfactory cosmetic properties (oily feel, break on application and lack of softness).

Generally, these emulsions additionally comprise a thickening agent, the function of which is to create, within the aqueous phase, a gelled matrix which serves to freeze the oily droplets and which provides for mechanical maintenance of the entire emulsion. However, the addition of such agents exerts the disadvantage of not making it possible to obtain all the desired textures, and in particular fluid and light textures which are easily and rapidly applied to the skin without leaving a residual film.

OBJECTS OF THE INVENTION

In view of this background, one object of the invention is the preparation of stable oil-in-water emulsions exhibiting good cosmetic qualities without having the disadvantages noted above, this being the case whatever the texture desired and in particular whatever the viscosity of the emulsion.

SUMMARY OF THE INVENTION

The inventors have discovered, unexpectedly, a novel family of polymers which makes it possible to prepare stable oil-in-water emulsions having very good cosmetic properties, whatever the texture envisaged, thus meeting the above object.

The present invention thus relates in one embodiment to a composition in the form of an oil-in-water emulsion comprising, preferably in a physiologically acceptable medium, an oily phase dispersed in an aqueous phase, wherein the aqueous phase comprises particles of uncrosslinked silicone copolymer and at least one amphiphilic surfactant capable of forming liquid crystals.

The composition of the invention may constitute, in particular, a composition for topical application, in particular a cosmetic or dermatological composition.

The term "amphiphilic surfactant capable of forming liquid crystals" as used herein is understood to mean any surfactant capable of giving rise to the formation of a liquid crystalline phase between 20 and 40° C., either in the composition itself at rest, or in the composition during the application of the composition to a keratinous substance, for example to the skin. Examples of these liquid crystal phases may be found in the work "Advances in Liquid Crystals", vol. 1, edited by Glenn H. Brown, 1995, pages 1 to 139.

The formation of liquid crystal line phases can be detected and demonstrated by cross polarization optical microscopy, optionally in combination with X-ray diffraction, and is within the skill of the ordinary artisan.

The liquid crystalline phases of the present invention are preferably of the direct or inverse, lamellar or hexagonal or cubic lyotropic type.

An O/W emulsion containing an aqueous suspension of particles of crosslinked organosiloxane elastomer is known from EP-A-1 097 703. However, the organosiloxane disclosed in this document is a crosslinked elastomer, whereas, in the present application, the silicone copolymer is neither an elastomer nor crosslinked but is a block copolymer, which is not the crosslinked organosiloxane of the document EP-A-1 097 703. In addition, the composition according to the invention has, surprisingly, the advantage over that described in EP-A-1 097 703 of being stable without the necessity of having to add thickening agents and thus of being without the disadvantages noted above. In addition, the cosmetic properties of the compositions according to the invention are better than those compositions comprising only silicone elastomer particles; in particular, the compositions of the invention exhibit greater softness and have less tendency to form blobs during application to the skin.

Furthermore, WO-A-97/32561 discloses O/W emulsions comprising a silicone phase comprising a polyorganosiloxane elastomer. However, the polyorganosiloxane used in this document is an elastomer and is therefore crosslinked, in contrast to the silicone copolymer of the present application. Furthermore, it is not in aqueous suspension but in the oily medium, and it is introduced into the oily phase and in particular the silicone phase of the emulsion and not into the aqueous phase, which has the disadvantage of having to follow, for the preparation of the compositions comprising compounds of this type, a highly specific and restrictive procedure, which is not the case for the copolymer used in the present application. In addition, when the polyorganosiloxane is in the oily phase, the compatibility with the other constituents is uncertain, in particular when silicone oil is concerned, and the stability is not assured.

The composition according to the present invention preferably has a homogeneous and pleasant texture on application. In addition, the dispersion of silicone copolymer particles used in the composition according to the invention make it possible to prepare oil-in-water emulsions which remain stable over time at ambient temperature or at higher temperatures and to retain these properties of the emulsion, whatever the fluidity of the emulsion. Thus, both thick emulsions, particularly effective for the treatment of dry skin, and very fluid emulsions, can therefore be prepared.

The viscosity of the invention emulsions can vary to a large extent. Viscosities can range for example from 0.05

Pa·s to 20 Pa·s, preferably from 0.05 to 10 Pa·s, including all values and subranges therebetween, these viscosities being measured at approximately (+/−10%) 25° C. using the "Rheomat 180" viscometer, which is generally equipped with a rotor 2 for viscosity ranges from 0.02 Pa·s to 0.7 Pa·s, with a rotor 3 for viscosity ranges from 0.2 Pa·s to 4 Pa·s, and with a rotor 4 for viscosity ranges from 2 P·s to 23 P·s.

The composition of the invention is provided in the form of an O/W emulsion. As it is useful for topical application, it preferably comprises a physiologically acceptable medium, that is to say a medium compatible with any keratinous substance, such as the skin, nails, mucous membranes and hair or any other cutaneous region of the body.

The composition can comprise dispersions of particles of one or more kinds of silicone copolymers. The silicone copolymer particles are present in the composition of the invention in concentrations which can vary widely. Preferably the concentration is adjusted according to the concentration of oil and according to the viscosity desired, and is within the skill of the ordinary worker in view of this disclosure. The concentration of silicone copolymer in the invention preferably ranges from 0.01 to 15% by weight, better still from 0.1 to 10% and even better still from 0.5 to 5% by weight with respect to the total weight of the composition, these ranges including all values and subranges therebetween.

The size of the silicone copolymer particles is not limited. Preferably, in the present invention the silicone copolymer particles generally exhibit a number-average size of less than or equal to 2 microns and preferably of less than or equal to 1 micron.

The dispersions of silicone copolymer particles used according to the invention include those disclosed in U.S. Pat. No. 6,013,682, incorporated herein by reference. According to this document, the silicone copolymers of these dispersions (particles) can be obtained in particular by a chain-extension reaction in the presence of a catalyst starting from at least:
  (a) one polysiloxane (i) having at least one reactive group and preferably one or two reactive groups per molecule; and
  (b) one organosilicone compound (ii) which reacts with the polysiloxane (i) by a chain-extension reaction.

In particular, the polysiloxane (i) is preferably chosen from the compounds of formula (I):

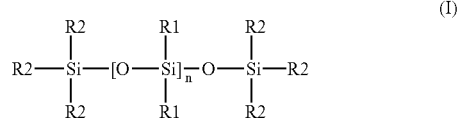

in which $R_1$ and $R_2$, independently of one another, represent a hydrocarbon group having from 1 to 20 carbon atoms, such as methyl, ethyl, propyl or butyl, or an aryl group, such as phenyl, or a reactive group and n is an integer greater than 1, provided that there are, on average, between one and two reactive groups per polymer.

The term "reactive group" is understood to mean any group capable of reacting with the compound (ii) to form a block copolymer. Useful reactive groups include hydrogen; aliphatically unsaturated groups, i.e. ethylenically unsaturated, i.e. having at least a double bond carbon-carbon, and in particular vinyl, allyl or hexenyl groups; the hydroxyl group; linear or branched alkoxy groups having 1 to 20 carbon atoms and preferably 1 to 6 carbon atoms, such as methoxy, ethoxy or propoxy groups; linear or branched alkoxyalkoxy groups having 1 to 20 carbon atoms and preferably 1 to 6 carbon atoms; the acetoxy group; amino groups, and their mixtures. Preferably, more than 90% and better still more than 98% of reactive groups are at the chain end, that is to say that the $R_2$ radicals generally constitute more than 90% and even 98% of the reactive groups.

Preferably, n is such that the polysiloxanes have a viscosity ranging from 1 to $1 \times 10^6$ mm$^2$/cm at 25° C.

The polysiloxanes of formula (I) are preferably substantially linear polymers, that is to say comprising few branchings, and generally less than 2 mol % of branchings in respect to the siloxane units. Furthermore, the $R_1$ and $R_2$ groups can optionally be substituted by amino groups, epoxy groups or groups comprising sulphur, silicon or oxygen.

Preferably, at least 80% of the $R_1$ groups are alkyl groups and better still methyl groups.

Preferably, the reactive group $R_2$ is an aliphatically unsaturated group and in particular a vinyl group.

Useful polysiloxanes (i) include dimethylvinylsiloxy-polydimethyl-siloxane, a compound of formula (I) in which the $R_1$ radicals are methyl radicals and, at the chain end, the $R_2$ radical is a vinyl radical, whereas the other two $R_2$ radicals are methyl radicals.

The organosilicone compound (ii) can be chosen from polysiloxanes of formula (I), preferably different from that used in (i), or compounds acting as chain-extending agent. If this is a compound of formula (I), the polysiloxane (i) will comprise a first reactive group and the organosilicone compound (ii) will comprise a second reactive group which will react with the first. If this is a chain of an extending agent, this can be a silane, a siloxane (disiloxane or trisiloxane) or a silazane. Preferably, the organosilicone compound (ii) is a liquid organohydropolysiloxane of formula (II):

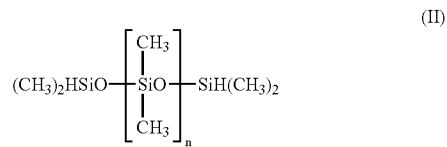

where n is an integer greater than 1 and preferably greater than 10 and, for example, ranging from 10 to 30. According to a specific embodiment of the invention, n is equal to 20.

The catalyst of the reaction between the polysiloxane (i) and the organosilicone compound (ii) can be chosen from metals and in particular from platinum, rhodium, tin, titanium, copper and lead. It is preferably platinum or rhodium.

The dispersions of silicone copolymer particles used according to the invention can be obtained in particular, for example, by mixing (a) water, (b) at least one emulsifier, (c) the polysiloxane (i), (d) the organosilicone compound (ii) and (e) a catalyst. Preferably, one of the constituents (c), (d) or (e) is added last to the mixture, in order for the chain-extension reaction to begin only in dispersion.

Mention may be made, as emulsifiers capable of being used in the preparation process described above for producing the aqueous dispersion of particles, of nonionic or ionic (anionic, cationic or amphoteric) emulsifiers. They are preferably nonionic emulsifiers which can be chosen from polyalkylene glycol ethers of a fatty alcohol comprising 8 to 30 carbon atoms and preferably from 10 to 22 carbon atoms; polyoxyalkylenated and in particular polyoxyethylenated alkyl esters of sorbitan, where the alkyl radical comprises from 8 to 30 carbon atoms and preferably from 10 to 22 carbon atoms; polyoxyalkylenated and in particular polyoxyethylenated alkyl esters, where the alkyl radical comprises from 8 to 30 carbon atoms and preferably from 10 to 22 carbon atoms; polyethylene glycols; polypropylene glycols; diethylene glycols; and their mixtures. The amount of emulsifier(s) is generally from 1 to 30% by weight with respect to the total weight of the reaction mixture.

The emulsifier used to obtain the aqueous dispersion of particles is preferably chosen from polyethylene glycol ethers of fatty alcohols and their mixtures and in particular polyethylene glycol ethers of alcohols comprising 12 or 13 carbon atoms and of 2 to 100 oxyethylene units and preferably of 3 to 50 oxyethylene units, and their mixtures. Mention may be made, for example, of $C_{12}$–$C_{13}$ Pareth-3, $C_{12}$–$C_{13}$ Pareth-23 and their mixtures.

According to a specific embodiment of the invention, the silicone copolymer particles are obtained from dimethylvinylsiloxypolydimethylsiloxane (or divinyl dimethicone) as compound (i) and from the compound of formula (II) as compound (ii), preferably in the presence of a catalyst of platinum type, and the dispersion of particles is preferably obtained in the presence of $C_{12}$–$C_{13}$ Pareth-3 and $C_{12}$–$C_{13}$ Pareth-23 as emulsifiers.

Use may in particular be made, as dispersion of silicone copolymer particles, of the product sold under the name HMW 2220 by Dow Corning CTFA (Cosmetics, Toiletry and Fragrance Association) name: divinyldimethicone/dimethicone/$C_{12}$–$C_{13}$ Pareth-3/$C_{12}$–$C_{13}$ Pareth-23). This raw material is a silicone in water emulstion where the oily globules (particles) are constituted from a silicone having a high viscosity such that the globules appear to form supple particles.

The composition of the invention preferably comprises at least one surfactant capable of forming liquid crystals. The amount of surfactant(s) capable of forming liquid crystals is not limited and can range, for example, from 0.05 to 20% by weight of active material and better still from 0.1 to 10% by weight of active material with respect to the total weight of the composition, all values and subranges between these limits being specifically included as if written out. Preferably, the composition comprises such surfactant(s) in an amount such that the composition comprises, either at rest, in use upon application to a keratinous substance, or both, a liquid crystalline phase. Such an amount, and whether a liquid crystalline phase is formed, is within the skill of the ordinary worker in view of this disclosure.

These surfactants can be chosen from anionic, cationic, amphoteric or nonionic surfactants and their mixtures. They can be liquid, semisolid or waxy and dispersible in water or in oil.

Use is preferably made of a surfactant having an HLB (Hydrophilic Lipophilic Balance) value ranging from 2 to 12 and preferably from 2 to 10.

The amphiphilic surfactants used in the composition of the invention comprise a lipophilic part and a hydrophilic part.

The lipophilic part preferably comprises at least one saturated or unsaturated and linear or branched chain having from 8 to 30 and preferably from 10 to 28 carbon atoms, such as the oleyl, lanolyl, tetradecyl, hexadecyl, isostearyl, lauryl, stearyl, acid from coconut oil or alkylphenyl chains.

When the hydrophilic part is a nonionic group, it can comprise a group chosen from oxyethylene chains (generally of 2 to 50 oxyethylene groups), polyglycerol groups, polyol groups, oxyalkylenated polyol groups and, for example, an oxyalkylenated and in particular oxyethylenated sugar or sorbitol group, and their mixtures. When the hydrophilic part is anionic, the latter can comprise a group chosen from the phosphate group, the phosphatidylcholine group and their mixtures.

The amphiphilic surfactants can, for example, be chosen from the following:

Nonionic Surfactants:
  Linear or branched polyglycerol alkyl ethers, such as, for example, Polyglyceryl-2 oleyl ether or Polyglyceryl-4 oleyl ether.
  Ethoxylated alkylphenols having an alkyl chain comprising from 8 to 26 carbon atoms, for example ethoxylated alkylphenols having an alkyl chain comprising 9 carbon atoms (CTFA name: Nonoxynol), such as Nonoxynol-2, for example the product sold under the name Igepal CO-210 by Rhône-Poulenc, and their mixtures.
  Esters of polyols derived from fatty acids comprising from 8 to 30 carbon atoms, and their oxyalkylenated and in particular oxyethylenated derivatives, the polyols preferably being chosen from sugars, $C_2$–$C_6$ alkylene glycols, glycerol, polyglycerols, sorbitol, sorbitan, polyethylene glycols, polypropylene glycols and their mixtures. The esters of polyols which are oxyalkylenated can comprise, for example, from 1 to 20 oxyalkylene groups and in particular 1 to 20 oxyethylene groups.

Mention may be made, as glycerol esters, of monoglycerides, such as monoolein (glyceryl oleate); monolinolein (glyceryl linoleate); monolaurin (glyceryl laurate), and their mixtures.

Mention may be made, as polyglycerol esters, of diglyceryl monoisostearate, diglyceryl oleate, triglyceryl monooleate, diglyceryl distearate, pentaglyceryl tristearate and their mixtures.

Mention may be made, as oxyethylenated glycerol ester, of, for example, oxyethylenated glycerol stearate comprising 20 oxyethylene units, such as the product sold under the name Tagat S by Goldschmidt.

Mention may be made, as sorbitan esters, of, for example, sorbitan stearate, such as the product sold under the name Span 60 by ICI, sorbitan laurate, such as the product sold under the name Span 20 by ICI, sorbitan palmitate, such as the product sold under the name Span 40 by ICI, sorbitan tristearate, such as the product sold under the name Span 65 by ICI, sorbitan oleate, such as the product sold under the name Span 80 by ICI, and sorbitan trioleate, such as the product sold under the name Span 85 by ICI. Mention may be made, as oxyethylenated sorbitan ester, of the Polysorbates and, for example, Polysorbate 21, sold under the name Tween 40 by ICI, and their mixtures.

Mention may be made, as sugar esters, of those derived from the following sugars: sucrose, glucose, fructose, mannose, galactose, arabinose, xylose, maltose, cellobiose, lactose, trehalose, raffinose or gentianose. Mention may be made, for example, of sucrose cocoate, sucrose monooctanoate, sucrose monodecanoate, sucrose monolaurate, sucrose monomyristate, sucrose monopalmitate, sucrose monostearate, sucrose monooleate, sucrose monolinoleate, sucrose dioleate, sucrose dipalmitate, sucrose distearate, sucrose dilaurate, sucrose dilinoleate, sucrose tristearate, esters of octyl-β-glucofuranoside, the Galactolipids sold by Scotia Lipid Teknik, and their mixtures.

Polyol ethers derived from alcohols comprising from 8 to 30 carbon atoms and in particular sugar ethers, such as glucose ethers, for example, in particular, alkylpolyglucosides (APG), such as decylglucoside ((C9/C11 alkyl)polyglucoside (1,4)) such as the product sold under the name Mydol 10 by Kao Chemicals or under the name Plantaren 2000 UP by Henkel; caprylyl/capryl glucoside, such as the product sold under the name Oramix CG 110 by Seppic; cetearyl glucoside, optionally as a mixture with cetearyl alcohol, sold, for example, under the name Montanov 68 by Seppic, under the name Tegocare CG90 by Goldschmidt and under the name Emulgade KE3302 by Cognis; arachidyl glucoside, for example in the form of a mixture with arachidyl and behenyl alcohols, a mixture sold under the name Montanov 202 by Seppic, and their mixtures.

Oxyethylenated silicones, such as the product sold under the name DC2-5695 by Dow Corning.

Block polymers of ethylene oxide and of propylene oxide, in particular Poloxamers such as Poloxamer 231, sold under the name Synperonic PE/L81 by Uniqema.

and their mixtures.

Anionic Surfactants

Carboxylic acids and salts of carboxylic acids comprising from 8 to 22 carbon atoms, preferably from 8 to 18 carbon atoms, such as potassium oleate, potassium laurate, potassium 10-undecenoate, potassium myristate, potassium palmitate and potassium stearate;

Esters and salts of phosphonic acid or of phosphoric acid, such as phospholipids, which may be natural and synthetic, phosphoglycerides, glycolipids, sphingolipids, for example ceramides, lecithin or lysolecithin;

Phosphoric acid diesters, such as sodium dioleyl phosphate;

Alkanesulphonates and their salts, such as 4-dodecylbenzenesulphonate;

Sulphosuccinates, such as dibutyl sodium sulphosuccinate or di(2-ethylhexyl) sodium sulphosuccinate;

Alkyl sulphates and their salts, such as lauryl sulphate and its salts;

Phosphatidylcholine derivatives, such as dioleylphosphatidylcholine;

and their mixtures.

Cationic Surfactants

Quaternary alkylimidazoline derivatives, such as alkyl (hydroxyethyl)imidazolinium chlorides and in particular stearyl(hydroxyethyl)imidazolinium chloride;

Ethoxylated amines, such as oxyethylenated alkylamines having an alkyl chain comprising at least 14 carbon atoms;

Alkylamines, such as dimethylalkylamines and their derivatives, for example the product sold under the name Armeen 18D by Akso Nobel, or dialkyldimethylamines and their derivatives, such as didodecyldimethylammonium bromide;

Quaternary alkylbenzyl derivatives, such as benzalkonium chloride;

and their mixtures.

Amphoteric and Zwitterionic Surfactants:

Alkyl betaines, such as oleyl betaine;

Alkylamidopropyl betaines, such as the cocamidopropyl betaine sold under the name Lebon 2000 HG by Sanyo;

and their mixtures.

Use may also be made of a mixture of one or more surfactants from different categories (anionic, cationic, nonionic, amphoteric or zwitterionic).

According to a preferred embodiment of the invention, the amphiphilic surfactant is chosen from nonionic surfactants, more particularly from polyol esters and ethers, oxyalkylenated polyol esters, or better still from sorbitan esters, sugar esters, sugar ethers, and their mixtures.

According to a specific embodiment of the invention, the amphiphilic surfactant comprises at least one sucrose ester chosen from sucrose cocoate, sucrose monooctanoate, sucrose monodecanoate, sucrose monolaurate, sucrose monomyristate, sucrose monopalmitate, sucrose monostearate, sucrose monooleate, sucrose monolinoleate, sucrose dioleate, sucrose dipalmitate, sucrose distearate, sucrose dilaurate, sucrose dilinoleate, sucrose tristearate, sucrose palmitate/stearate, and their mixtures.

According to another specific embodiment of the invention, the amphiphilic surfactant comprises at least one glucose ether chosen from alkylpolyglucosides.

Use may be made in particular, as examples of amphiphilic surfactants, of a mixture of cocoate sucrose and of sorbitan stearate, especially of the mixture of sucrose cocoate and of sorbitan stearate sold under the name Arlatone 2121 by ICI. Mention may also be made, as examples of amphiphilic surfactants, of the sucrose cocoate sold by Croda under the name Crodesta SL40; the sucrose stearates sold by Croda under the names Crodesta F160, F140, F110, F90 and F70, respectively denoting the sucrose palmitate/stearates formed of 73% monoester and 27% di- and triester, of 61% monoester and 39% di-, tri- and tetraester, of 52% monoester and 48% di-, tri- and tetraester, of 45% monoester and 55% di-, tri- and tetraester, and of 39% monoester and 61% di-, tri- and tetraester; sucrose monolaurate; sucrose monostearate; sucrose distearate; sucrose tristearate and their mixtures, such as the products sold by Croda under the names Crodesta F50, F70, F110 and F160, respectively having an HLB (Hydrophilic Lipophlic Balance) of 5, 7, 11 and 16; the sucrose behenate sold by Mitsubishi under the reference Ryoto Sugar ester B-370, formed of 20% monoester and 80% di-, tri- and polyester; the distearate of methyl glucose and of polyglycerol-3, sold by Goldschmidt under the name of Tegocare 450; methyl O-hexadecanoyl-6-D-glucoside; [lacuna] O-hexadecanoyl-6-D-maltoside; Sucrose polycottonseedate (CTFA name); and their mixtures.

The amphiphilic surfactant can be composed of a mixture of these various preferred surfactants.

The aqueous phase of the compositions according to the invention comprises at least water. The amount of aqueous phase generally ranges from 40 to 99% by weight with respect to the total weight of the composition and preferably from 60 to 95% by weight with respect to the total weight of the composition. The amount of water can represent all or a portion of the aqueous phase and is generally at least 30% by weight with respect to the total weight of the composition.

The compositions of the invention can comprise, in the aqueous phase or in the oily phase, one or more hydrophilic, lipophilic and/or amphiphilic organic solvents which are preferably physiologically acceptable, that is to say well tolerated and giving a cosmetically acceptable feel.

The organic solvents can represent from 1 to 50% and preferably from 2 to 20% of the total weight of the composition. The organic solvents can be preferably chosen from the group consisting of hydrophilic organic solvents, lipophilic organic solvents, amphiphilic solvents, and their mixtures.

Mention may be made, among organic solvents, of, for example, linear or branched lower monoalcohols having from 1 to 8 carbon atoms, such as ethanol, propanol, butanol, isopropanol or isobutanol; polyols, such as propylene glycol, isoprene glycol, butylene glycol, glycerol or sorbitol; mono- or dialkyl isosorbide, the alkyl groups of which have from 1 to 5 carbon atoms, such as dimethyl isosorbide; polyethylene glycols, in particular those having from 6 to 80 ethylene oxides; ethylene glycol ethers, such as diethylene glycol monomethyl or monethyl ether; propylene glycol ethers such as dipropylene glycol methyl ether; polyol esters and ethers, such as polypropylene glycol (PPG) esters and more especially esters of polypropylene glycol (PPG) and of a fatty acid or ethers of PPG and of a fatty alcohol, such as PPG-23 oleyl ether and PPG-36 oleate; fatty acid esters, such as diisopropyl adipate or dioctyl adipate; alkyl benzoates; and their mixtures.

The oily phase of the composition according to the invention generally represents from 3 to 60% and preferably from 5 to 30% by weight with respect to the total weight of the composition, all values and subranges between these limits being included as if specifically written out.

The nature of the oily phase of the emulsion according to the invention is not critical. The oily phase can thus be composed of any fatty substance and in particular oil conventionally used in the cosmetics or dermatological fields. The oily phase generally comprises at least one oil.

Mention may be made, as oils which can be used in the composition of the invention, of, for example:

- hydrocarbonaceous oils of animal origin, such as perhydrosqualene;
- hydrocarbonaceous oils of vegetable origin, such as liquid triglycerides of fatty acids comprising from 4 to 10 carbon atoms, such as triglycerides of heptanoic or octanoic acids or, for example, sunflower, maize, soybean, cucumber, grape seed, sesame, hazelnut, apricot, macadamia, arara, sunflower, castor or avocado oils, triglycerides of caprylic/capric acids, such as those sold by Stearineries Dubois or those sold under the names Miglyol 810, 812 and 818 by Dynamit Nobel, jojoba oil or karite butter oil;
- synthetic esters and ethers, in particular of fatty acids, such as the oils of formulae $R^aCOOR^b$ and $R^aOR^b$ in which $R^a$ represents the residue of a fatty acid comprising from 8 to 29 carbon atoms and $R^b$ represents a branched or unbranched hydrocarbonaceous chain comprising from 3 to 30 carbon atoms, such as, for example, Purcellin oil, isononyl isononanoate, isopropyl myristate, 2-ethylhexyl palmitate, 2-octyldodecyl stearate, 2-octyldodecyl erucate or isostearyl isostearate; hydroxylated esters, such as isostearyl lactate, octyl hydroxystearate, octyldodecyl hydroxystearate, diisostearyl malate, triisocetyl citrate, or heptanoates, octanoates or decanoates of fatty alcohols; polyol esters, such as propylene glycol dioctanoate, neopentyl glycol diheptanoate and diethylene glycol diisononanoate; and pentaerythritol esters, such as pentaerythrityl tetraisostearate;
- linear or branched hydrocarbons of mineral or synthetic origin, such as liquid paraffins, which may or may not be volatile, and their derivatives, liquid petrolatum, polydecenes or hydrogenated polyisobutene, such as parleam oil;
- fatty alcohols having from 8 to 26 carbon atoms, such as cetyl alcohol, stearyl alcohol and their mixture (cetearyl alcohol), octyldodecanol, 2-butyloctanol, 2-hexyldecanol, 2-undecylpentadecanol, oleyl alcohol or linoleyl alcohol;
- alkoxylated and in particular ethoxylated fatty alcohols, such as oleth-12, ceteareth-12 and ceteareth-20;
- partially hydrocarbonaceous and/or silicone-comprising fluorinated oils, such as those disclosed in the document JP-A-2-295912. Mention may also be made, as fluorinated oils, of perfluoromethylcyclopentane and perfluoro(1,3-dimethylcyclohexane), sold under the names of "FLUTEC PC1®" and "FLUTEC PC3®" by BNFL Fluorochemicals; perfluoro(1,2-dimethylcyclobutane); perfluoroalkanes, such as dodecafluoropentane and tetradecafluorohexane, sold under the names of "PF 5050®" and "PF 5060®" by 3M, or bromoperfluorooctane, sold under the name "FORALKYL®", by Atochem; nonafluoromethoxybutane, sold under the name "MSX 4518®" by 3M, and nonafluoroethoxyisobutane; or perfluoromorpholine derivatives, such as 4-(trifluoromethyl)perfluoromorpholine, sold under the name "PF 5052®" by 3M;
- silicone oils, such as volatile or nonvolatile polymethylsiloxanes (PDMS) comprising a linear or cyclic silicone chain which are liquid or pasty at ambient temperature, in particular cyclopolydimethylsiloxanes (cyclomethicones), such as cyclohexasiloxane; polydimethylsiloxanes comprising pendant alkyl, alkoxy or phenyl groups or alkyl, alkoxy or phenyl groups at the silicone chain end, which groups have from 2 to 24 carbon atoms; or phenylated silicones, such as phenyltrimethicones, phenyldimethicones, phenyltrimethylsiloxydiphenylsiloxanes, diphenyl dimethicones, diphenylmethyldiphenyltrisiloxanes, (2-phenylethyl)trimethylsiloxysilicates and polymethylphenylsiloxanes;
- their mixtures.

The term "hydrocarbonaceous oil" in the list of the oils mentioned above is understood to mean any oil comprising predominantly carbon and hydrogen atoms and optionally ester, ether, fluorinated, carboxylic acid and/or alcohol groups.

The other fatty substances which can be present in the oily phase are, for example, fatty acids comprising from 8 to 30 carbon atoms, such as stearic acid, lauric acid, palmitic acid and oleic acid; waxes, such as lanolin wax, beeswax, carnauba or candelilla wax, paraffin or lignite waxes or microcrystalline waxes, ceresin or ozokerite, or synthetic waxes, such as polyethylene waxes or Fischer-Tropsch waxes; gums, such as silicone gums (dimethiconol); or silicone resins, such as trifluoromethyl $C_{1-4}$ alkyl dimethicone and trifluoropropyldimethicone.

These fatty substances can be chosen in a way within the skill of persons skilled in the art in order to prepare a composition having the desired properties, for example of consistency or of texture, in view of this disclosure.

According to a specific embodiment of the invention, the composition of the invention comprises at least one silicone oil, preferably a volatile silicone oil, which can be chosen, for example, from cyclic or linear polydimethylsiloxanes, and their mixtures. The cyclic polydimethylsiloxanes or cyclomethicones comprise from approximately 3 to 9 silicon atoms and preferably from 4 to 6 silicon atoms and can be, for example, cyclohexadimethylsiloxane and cyclopentadimethylsiloxane. The volatile linear polydimethylsiloxanes preferably comprise from approximately 3 to 9 silicon atoms. The volatile linear polydimethylsiloxanes generally have a viscosity at 25° C. of less than or equal to 5 cSt while the cyclomethicones generally have a viscosity at 25° C. of less than or equal to 10 cSt.

The compositions of the invention can comprise one or more of adjuvants known to be used in the cosmetics and dermatological fields, such as hydrophilic or lipophilic gelling and/or thickening agents; moisturizing agents; emollients; hydrophilic or lipophilic active principles; agents for combating free radicals; sequestering agents; antioxidants; preservatives; basifying or acidifying agents; fragrances; pigments; film-forming agents; colouring materials; and their mixtures.

The amounts of these various adjuvants are those conventionally used in the fields under consideration, which amounts are known or determinable by those of ordinary skill in view of this disclosure.

Examples of gelling agents that can be used include hydrophilic polymers, such as carboxyvinyl polymers, for example carbomers; polysaccharides, such as guar gum or xanthan gum, and cellulose derivatives, such as, for example, hydroxyethylcellulose; or water-soluble or water-dispersible silicone derivatives, such as acrylic silicones and cationic silicones. Use may also be made of lipophilic gelling agents, such as modified clays or modified polysaccharides.

Examples of active principles which can be used in the composition of the invention include moisturizing agents, such as protein hydrolysates and polyols, such as glycerol, glycols, such as polyethylene glycols, and sugar derivatives; natural extracts; anti-inflammatories; procyanidol oligomers; vitamins, such as vitamin A (retinol), vitamin E (tocopherol), vitamin B5 (panthenol), vitamin B3 (niacinamide), the derivatives of these vitamins (in particular esters), and their mixtures; urea; caffeine; depigmenting agents, such as kojic acid, hydroquinone and caffeic acid; salicylic acid and its derivatives; α-hydroxy acids, such as lactic acid and glycolic acid, and their derivatives; retinoids, such as carotenoids and vitamin A derivatives; sunscreen agents; hydrocortisone; melatonin; extracts of algae, of fungi, of plants, of yeasts or of bacteria; enzymes; steroids; antibacterial active principles, such as 2,4,4'-trichloro-2'-hydroxydiphenyl ether (or triclosan), 3,4,4'-trichlorocarbanilide (or triclocarban) and the acids indicated above and in particular salicylic acid and its derivatives; mattifying agents, such as fibres; tightening agents; and their mixtures.

Examples of steroids useful herein include dehydroepiandrosterone (or DHEA) and (1) its biological derivatives and precursors, in particular DHEA salts and esters, such as DHEA sulphate and salicylate, 7-hydroxy-DHEA, 7-keto-DHEA, or 7-hydroxy- and 7-keto-DHEA esters, in particular 3-β-acetoxy-7-oxo-DHEA, and (2) its chemical derivatives and precursors, in particular sapogenins such as diosgenin or hecogenin, and/or their derivatives, such as hecogenin acetate, and/or the natural extracts comprising them and in particular extracts of Dioscorea species, such as wild yam.

Useful sunscreen agents (or UV screening agents) include organic screening agents, physical screening agents and their mixtures.

The composition of the invention can comprise, as chemical sunscreen agents which can be used in the composition of the invention, any UVA and UVB screening agent which can be used in the cosmetics field.

Mention may be made, as useful UVB screening agents, of, for example:
(1) salicylic acid derivatives, in particular homomenthyl salicylate and octyl salicylate;
(2) cinnamic acid derivatives, in particular 2-ethylhexyl p-methoxycinnamate, sold by Givaudan under the name Parsol MCX;
(3) liquid β,β-diphenylacrylate derivatives, in particular 2-ethylhexyl α-cyano-β,β-diphenylacrylate or octocrylene, sold by BASF under the name UVINUL N539;
(4) p-aminobenzoic acid derivatives;
(5) 4-methylbenzylidenecamphor, sold by Merck under the name Eusolex 6300;
(6) 2-phenylbenzimidazole-5-sulphonic acid, sold under the name Eusolex 232 by Merck;
(7) 1,3,5-triazine derivatives, in particular:
2,4,6-tris[p-(2'-ethylhexyl-1'-oxycarbonyl)anilino]-1,3,5-triazine, sold by BASF under the name Uvinul T150, and
dioctyl butamido triazone, sold by Sigma 3V under the name Uvasorb HEB;
(8) the mixtures of these screening agents.

Mention may be made, as useful UVA screening agents, of, for example:
(1) dibenzolymethane derivatives, in particular 4-(tert-butyl)-4',-methoxydibenzoylmethane, sold by Givaudan under the name Parsol 1789;
(2) benzene-1,4-[di(3-methylidenecamphor-10-sulphonic acid)], optionally in the partially or completely neutralized form, sold under the name Mexoryl SX by Chimex;
(3) benzophenone derivatives, for example:
2,4-dihydroxybenzophenone (benzophenone-1);
2,2',4,4'-tetrahydroxybenzophenone (benzophenone-2);
2-hydroxy-4-methoxybenzophenone (benzophenone-3), sold under the name Uvinul M40 by BASF;
2-hydroxy-4-methoxybenzophenone-5-sulphonic acid (benzophenone-4), and its sulphonate form (benzophenone-5), sold by BASF under the name Uvinul MS40;
2,2'-dihydroxy-4,4'-dimethoxybenzophenone (benzophenone-6);
5-chloro-2-hydroxybenzophenone (benzophenone-7);
2,2'-dihydroxy-4-methoxybenzophenone (benzophenone-8);
the disodium salt of 2,2'-dihydroxy-4,4'-dimethoxybenzophenone-5,5'-disulphonic diacid (benzophenone-9);
2-hydroxy-4-methoxy-4'-methylbenzophenone (benzophenone-10);
benzophenone-11;
2-hydroxy-4-(octyloxy)benzophenone (benzophenone-12);
(4) silane derivatives or polyorganosiloxanes comprising a benzophenone group;
(5) anthranilates, in particular menthyl anthranilate, sold by Haarmann & Reimer under the name Neo Heliopan MA;
(6) compounds comprising, per molecule, at least two benzazolyl groups or at least one benzodiazolyl group, in particular 1,4-bis-benzimidazolyl-phenylene-3,3',5,5'-tetrasulphonic acid, and its salts, sold by Haarmann & Reimer;
(7) silicon derivatives of N-substituted benzimidazolyl-benzazoles or of benzofuranyl-benzazoles, and in particular:
2-[1-[3-[1,3,3,3-tetramethyl-1-[(trimethylsilyl)oxy]disiloxanyl]propyl]-1H-benzimidazol-2-yl]benzoxazole;
2-[1-[3-[1,3,3,3-tetramethyl-1-[(trimethylsilyl)oxy]disiloxanyl]propyl]-1H-benzimidazol-2-yl]benzothiazole;
2-[1-(3-(trimethylsilanyl)propyl)-1H-benzimidazole-2-yl]benzoxazole;
6-methoxy-1,1'-bis(3-(trimethylsilanyl)propyl)-1H,1'H-[2,2']bibenzimidazolyl-benzoxazole;
2-[1-(3-(trimethylsilanyl)propyl)-1H-benzimidazol-2-yl] benzothiazole;

which are disclosed in Patent Application EP-A-1 028 120;
(8) triazine derivatives and in particular 2,4-bis[4-(2-ethyl-hexyloxy)-2-hydroxyphenyl]-6-(4-methoxyphenyl)-1,3, 5-triazine, sold by Ciba Geigy under the name Tinosorb S, and 2,2'-methylenebis[6-(2H-benzotriazol-2-yl)-4-(1,1,3, 3-tetramethylbutyl)phenol], sold by Ciba Geigy under the name Tinosorb M;
(9) their mixtures.

Use may also be made of a mixture of two or several of these screening agents and a mixture of UVB screening agents and of UVA screening agents and also mixtures with physical screening agents.

Useful physical screening agents include titanium oxide (amorphous titanium dioxide or crystalline titanium dioxide in the rutile and/or anatase form), zinc oxide, iron oxide, zirconium oxide, cerium oxide or their mixtures. These metal oxides can be in the form of particles having a micrometric size or nanometric size (nanopigments). In the form of nanopigments, the mean sizes of the particles range, for example, from 5 to 100 nm. Use is preferably made, in the composition of the invention, of nanopigments.

These pigments may, furthermore, be used in particular in make-up compositions, optionally after having been treated so as to render their surface hydrophobic; this treatment can be carried out according to methods known to a person skilled in the art; the pigments can in particular be coated with silicone compounds, such as PDMSs and/or with polymers.

Of course, a person skilled in the art will preferably take care to choose the optional adjuvant or adjuvants added to the composition according to the invention so that the advantageous properties intrinsically attached to the composition in accordance with the invention are not, or not substantially, detrimentally affected by the envisaged addition.

The compositions according to the invention can be provided in any form including in the form of gels, of lotions, of milks, of more or less smooth creams or of pastes. These compositions can be prepared according to conventional methods, within the skill of the ordinary worker in view of this disclosure.

The composition preferably exhibits a pH which does not harm the skin and which generally ranges from 3 to 8 and preferably from 4.5 to 7, all values and subranges between these values being included as if specifically written out.

The compositions of the invention can be used as a product for caring for, treating, protecting, cleaning, removing make-up from and/or making-up keratinous substances (skin, hair, scalp, eyelashes, eyebrows, nails or mucous membranes), such as protection, treatment or care creams for the face, for the hands or for the body, protection or care body milks, or gels or foams for caring for the skin and/or mucous membranes (lips).

The compositions of the invention can comprise sunscreen agents and can thus also be used as a sun protection product.

The compositions can be used as make-up products, in particular for making-up the skin, eyebrows, eyelashes and lips, such as face creams, foundations, mascaras or lipsticks. Such products generally comprise pigments.

The compositions according to the invention can also be used as rinse-out products or as leave-in products for cleaning the skin of the face and/or of the body and/or for cleaning the hair, for example as hair products, including for caring for and conditioning the hair.

In view of this disclosure and the Exampples that follow the following specific embodiments are enabled such that they can be made and used by those of ordinary skill in the art:

The cosmetic use of a composition as defined above as rinse-out or leave-in hair product.

The cosmetic use of a composition as defined above as product for cleaning and/or removing make-up from the skin and/or eyes.

The cosmetic use of a composition as defined above as product for caring for the skin, hair, scalp, eyelashes, eyebrows, nails or mucous membranes.

The cosmetic use of a composition as defined above as make-up product.

The cosmetic use of a composition as defined herein as sun protection product (protection against the sun and/or the UV radiation from tanning devices).

The cosmetic treatment of a keratinous substance (skin, scalp, hair, eyelashes, eyebrows, nails or mucous membranes), wherein a composition as defined herein is applied to the keratinous substance, where the keratinous substance is in particular the skin.

A composition in the form of an oil-in-water emulsion comprising, in a physiologically acceptable medium, an oily phase dispersed in an aqueous phase, wherein the aqueous phase comprises particles of uncrosslinked silicone copolymer and at least one amphiphilic surfactant capable of forming liquid crystals.

A composition in the form of an oil-in-water emulsion comprising, in a physiologically acceptable medium, an oily phase dispersed in an aqueous phase, wherein the aqueous phase comprises particles of uncrosslinked silicone copolymer and at least one amphiphilic surfactant capable of forming a liquid crystalline phase in an amount such that the composition comprises a liquid crystalline phase either at rest, upon use in application to a keratinous substance, or both.

The cosmetic use of a composition according to the invention for caring for the skin, hair, scalp, eyelashes, eyebrows, nails or mucous membranes, as make-up product, as sun protection product, as rinse-out or leave-in hair product, as product for cleaning and/or removing make-up from the skin and/or eyes, for the cosmetic treatment of a keratinous substance.

The examples which follow will make possible a better understanding of the invention, without, however, exhibiting a limiting nature. The amounts shown are as % by weight, unless otherwise mentioned.

EXAMPLE 1

Cream

| Phase A (oily phase) | |
|---|---|
| Mixture of cocoyl polyglucoside and of cetyl, stearyl alcohol (35/65) (Montanov 82 from Seppic) | 3% |
| Soybean oil | 10% |
| Cyclohexadimethylsiloxane | 5% |
| Liquid petrolatum | 10% |
| Stearic acid | 0.5% |
| Phase B (aqueous phase) | |
| Glycerol | 5% |
| Carbomer | 0.5% |
| Triethanolamine | 0.5% |

-continued

| | |
|---|---|
| Water | q.s. for 100% |
| Phase C | |
| HMW2220 (Dow Corning) | 2% |
| Fragrance | 0.1% |

Procedure: Phase B is prepared under hot conditions with stirring. Phase A is added thereto. The mixture is cooled and then phase C is added with low shearing of the dispersion.

A white cream is obtained which is very soft on application without a greasy feel and which gives a good feeling of moisturization after application.

EXAMPLE 2

Cream

| | |
|---|---|
| Phase A (oily phase) | |
| Sucrose mono- and dipalmitate/stearate (Tegosoft PSE 141 G from Goldschmidt) | 2% |
| Stearyl alcohol | 1% |
| Cyclohexadimethylsiloxane | 2% |
| Isohexadecane | 5% |
| Stearic acid | 0.5% |
| Phase B (aqueous phase) | |
| Glycerol | 5% |
| Carbomer | 0.5% |
| Triethanolamine | 0.5% |
| Water | q.s. for 100% |
| Phase C | |
| HMW2220 (Dow Corning) | 4% |
| Fragrance | 0.1% |

Procedure: Phase B is prepared under hot conditions with stirring. Phase A is added thereto. The mixture is cooled and then phase C is added with low shearing of the dispersion.

A white cream is obtained which is very soft on application without a greasy feel and which gives a good feeling of moisturization after application.

EXAMPLE 3

Sprayable Fluid

| | |
|---|---|
| Phase A (oily phase) | |
| Volatile silicone | 10% |
| Mineral oil | 10% |
| Lecithin | 3% |
| Hydrogenated lecithin | 1% |
| Phase B (aqueous phase) | |
| Glycerol | 5% |
| Water | q.s. for 100% |
| Preservative | q.s. |
| Phase C | |
| HMW2220 (Dow Corning) | 2% |
| Fragrance | 0.1% |

Procedure: The lecithins are dissolved in the fatty phase under hot conditions (70° C.) with stirring. Furthermore, the aqueous phase is prepared under hot conditions. Phase A is poured into phase B and a pre-emulsion prepared with stirring. The pre-emulsion is passed into a high-pressure device (500 bar, 2 passes). The mixture is cooled and then phase C is added with gentle stirring.

A fluid is obtained which is very fresh and light on application and which leaves the skin soft and matt with a good feeling of moisturization. This fluid can be applied directly or by spraying, as can all invention compositions herein, the preferable application method being with the fingers.

French patent application 0113272 filed Oct. 15, 2001, is incorporated here by reference, as are all references, texts, documents, patents, applications, tests, product brochures, etc., mentioned herein. Where numerical ranges are given, all values and subranges between stated values are included as if specifically written out. As noted above, the term "approximately" means ±10%.

The invention claimed is:

1. A composition in the form of an oil-in-water emulsion comprising an oily phase dispersed in an aqueous phase, wherein the aqueous phase comprises a dispersion of particles of uncrosslinked silicone copolymer, and at least one amphiphilic surfactant capable of forming liquid crystals, wherein said surfactant is present in an amount sufficient to form a liquid crystalline phase within the composition at rest, within the composition upon application to a keratinous substance, or both, wherein the silicone copolymer is obtained by a chain-extension reaction in the presence of a catalyst starting from at least:
   (a) one polysiloxane (i) having at least one reactive group per molecule, wherein the polysiloxane (i) is selected from the group consisting of formula (I):

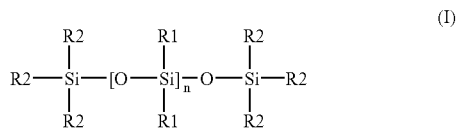

in which $R_1$ and $R_2$, independently of one another, represent a hydrocarbonaceous group having from 1 to 20 carbon atoms or an aryl group or a reactive group and n, in formula (I), is an integer greater than 1, provided that there are, on average, between one and two reactive groups per polymer; and
   (b) one organosilicone compound (ii) which reacts with the polysiloxane (i) by a chain-extension reaction, wherein the organosilicone compound (ii) is a liquid organohydropolysiloxane of formula (II):

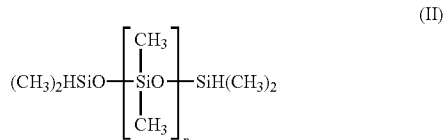

where n, in formula (II), is an integer greater than 1.

2. The composition according to claim 1, wherein the dispersion of silicone copolymer particles is obtained by mixing water, at least one emulsifier, polysiloxane (i), organosilicone compound (ii) and a catalyst.

3. The composition according to claim 2, wherein the emulsifier is a nonionic emulsifier selected from the group consisting of polyalkylene glycol ethers of a fatty alcohol comprising from 8 to 30 carbon atoms; polyoxyalkylenated alkyl esters of sorbitan, where the alkyl radical comprises from 8 to 30 carbon atoms; polyoxyalkylenated alkyl esters, where the alkyl radical comprises from 8 to 30 carbon atoms; polyethylene glycols; polypropylene glycols; diethylene glycols; and their mixtures.

4. The composition according to claim 2, wherein the emulsifier is selected from the group consisting of polyethylene glycol ethers of alcohols comprising 12 or 13 carbon atoms and of 3 to 50 oxyethylene units, and their mixtures.

5. The composition according to claim 1, further comprising one or more organic solvents.

6. The composition according to claim 5, wherein the organic solvent is selected from the group consisting of linear or branched lower monoalcohols having from 1 to 8 carbon atoms; polyols; mono- or dialkyl isosorbide, the alkyl groups of which have from 1 to 5 carbon atoms; polyethylene glycols having from 6 to 80 ethylene oxides; ethylene glycol ethers; propylene glycol ethers; polyol esters and ethers; fatty acid esters; and their mixtures.

7. The composition according to claim 5, wherein the amount of organic solvent(s) present ranges from 2 to 50% by weight with respect to the total weight of the composition.

8. The composition according to claim 1, wherein the amount of amphiphilic surfactant(s) present ranges from 0.05 to 20% by weight with respect to the total weight of the composition.

9. The composition according to claim 8, wherein the amphiphilic surfactant is selected from the group consisting of anionic, cationic, amphoteric, nonionic surfactants and their mixtures.

10. The composition according to claim 1, wherein the amphiphilic surfactant comprises a hydrophilic part and a lipophilic part comprising a saturated or unsaturated and linear or branched chain having from 8 to 30 carbon atoms.

11. The composition according to claim 10, wherein the hydrophilic part of the amphiphilic surfactant comprises an oxyethylene group, polyglycerol group, polyol group, oxyalkylenated polyol group, or mixture thereof.

12. The composition according to claim 1, wherein the oily phase is present from 3 to 60% by weight with respect to the total weight of the composition.

13. The composition according to claim 12, wherein the oily phase comprises at least one volatile silicone oil.

14. The composition according to claim 1, wherein it constitutes a product for caring for, treating, protecting, cleaning, removing make-up from and/or making-up keratinous substances.

15. The composition according to claim 14, wherein the keratinous substance is the skin.

16. A process for the treatment of a keratinous substance, comprising applying the composition of claim 1 to the keratinous substance.

17. A process according to claim 16, wherein the keratinous substance is skin.

18. The composition according to claim 1, wherein the amount of silicone copolymer present ranges from 0.01 to 15% by weight with respect to the total weight of the composition.

19. The composition according to claim 1, wherein the silicone copolymer particles have a number-average size of less than or equal to 2 microns.

20. The composition according to claim 1, wherein the reactive groups are selected from the group consisting of hydrogen; aliphatically unsaturated groups; the hydroxyl group; alkoxy groups; alkoxyalkoxy groups; the acetoxy group; amino groups; and their mixtures.

21. The composition according to claim 1, wherein $R_1$ represents a methyl group.

22. The composition according to claim 1, wherein $R_2$ represents a vinyl group.

23. The composition according to claim 1, wherein, in the formula (II), n is equal to 20.

24. The composition according to claim 1, wherein the silicone copolymer particles are obtained from dimethylvinylsiloxypolydimethylsiloxane and from the compound of formula (II).

25. The composition according to claim 1, wherein the amphiphilic surfactant is a nonionic surfactant selected from the group consisting of polyglycerol alkyl ethers; ethoxylated alkylphenols; polyol esters and their oxyalkylenated derivatives; ethers of fatty alcohols and of a sugar; oxyethylenated silicones; block polymers of ethylene oxide and of propylene oxide; and their mixtures.

26. The composition according to claim 1, wherein the amphiphilic surfactant is an anionic surfactant selected from the group consisting of carboxylic acids and salts of carboxylic acids comprising from 8 to 22 carbon atoms; esters and salts of phosphonic acid or of phosphoric acid; phosphoric acid diesters; alkanesulphonates and their salts; sulphosuccinates; alkyl sulphates and their salts; phosphatidylcholine derivatives; and their mixtures.

27. The composition according to claim 1, wherein the amphiphilic surfactant is a cationic surfactant selected from the group consisting of quaternary alkylimidazoline derivatives; ethoxylated amines; alkylamines; quaternary alkylbenzyl derivatives; and their mixtures.

28. The composition according to claim 1, wherein the amphiphilic surfactant is an amphoteric or zwitterionic surfactant selected from the group consisting of alkyl betaines, alkylamidopropyl betaines; and their mixtures.

29. The composition according to claim 1, wherein the amphiphilic surfactant is selected from the group consisting of sugar esters, sugar ethers, sorbitan esters and their mixtures.

30. The composition according to claim 1, comprising at least one sucrose ester selected from the group consisting of sucrose cocoate, sucrose monooctanoate, sucrose monodecanoate, sucrose monolaurate, sucrose monomyristate, sucrose monopalmitate, sucrose monostearate, sucrose monooleate, sucrose monolinoleate, sucrose dioleate, sucrose dipalmitate, sucrose distearate, sucrose dilaurate, sucrose dilinoleate, sucrose tristearate, sucrose palmitate/stearate, and their mixtures.

31. The composition according to claim 1, wherein the amphiphilic surfactant is a mixture of sorbitan stearate and sucrose cocoate.

32. The composition according to claim 1, wherein the amphiphilic surfactant comprises at least one glucose ether selected from the group consisting of alkylpolyglucosides.

33. The composition according to claim 1, wherein the aqueous phase is present from 40 to 99% by weight with respect to the total weight of the composition.

34. The composition according to claim 1, further comprising one or more adjuvants selected from the group consisting of from gelling agents; moisturizing agents; emollients; active principles; agents for combating free radicals; sequestering agents; antioxidants; preservatives; basifying or acidifying agents; fragrances; pigments; film-forming agents; colouring materials; and their mixtures.

35. The composition according to claim 1, wherein it constitutes a cosmetic or dermatological composition.

36. A method for caring for, making up, or protecting from the sun the skin, hair, scalp, eyelashes, eyebrows, nails or mucous membranes, comprising applying the composition of claim 1 to the skin, hair, scalp, eyelashes, eyebrows, nails or mucous membranes.

37. A method for cleaning and/or removing make-up from the skin and/or eyes, comprising applying the composition of claim 1 to made-up skin and/or eyes.

38. The composition according to claim 1, wherein, in the formula (II), n is greater than 10.

* * * * *